United States Patent [19]

DeMarco et al.

[11] Patent Number: 5,186,929
[45] Date of Patent: Feb. 16, 1993

[54] TREATING PROTEINACEOUS SUBSTRATES WITH CATIONIC COPOLYMER

[75] Inventors: Richard DeMarco, Danbury; Raymond Feinland, Stamford; Janusz Jachowicz, Bethel, all of Conn.

[73] Assignee: Clairol, Incorporated, New York, N.Y.

[21] Appl. No.: 598,571

[22] Filed: Oct. 16, 1990

Related U.S. Application Data

[63] Continuation of Ser. No. 240,787, Sep. 2, 1988, abandoned.

[51] Int. Cl.$^5$ .......................... A61K 7/06; A61K 7/09
[52] U.S. Cl. ........................................ 424/71; 424/70; 424/78.08; 8/127.51; 8/127.6; 8/188; 8/405; 252/8.8
[58] Field of Search .......................... 424/81, 70, 71; 252/8.8; 8/127.6, 127.51, 94.14, 94.18, 405, 606, 901, 916

[56] References Cited

U.S. PATENT DOCUMENTS

| 4,438,095 | 3/1984 | Grollier et al. | 424/78 X |
| 4,460,567 | 7/1984 | Strasilla et al. | 424/70 |
| 4,645,663 | 2/1987 | Grollier et al. | 424/81 X |
| 4,818,245 | 4/1989 | Jachowicz | 424/70 X |

OTHER PUBLICATIONS

J. Jachowicz et al., Textile Research Journal, vol. 57, No. 9, Sep. 1987, pp. 543-548.

*Primary Examiner*—Thurman K. Page
*Assistant Examiner*—James M. Spear
*Attorney, Agent, or Firm*—Anthony M. Santini; Charles J. Zeller

[57] ABSTRACT

The treatment of proteinaceous or other substrates to render them more manageable and more stable against chemical treatment involves the use of aqueous compositions containing cationic (meth)acrylic copolymers.

6 Claims, No Drawings

TREATING PROTEINACEOUS SUBSTRATES WITH CATIONIC COPOLYMER

This application is a continuation of application Ser. No. 07/240,787, filed Sep. 2, 1988 now abandoned.

BACKGROUND

Chemical processing such as the coloring, straightening and permanent waving of human hair and other proteinaceous substrates can be damaging to those substrates. It is known in the art to protect or, in some respects, "stabilize" the hair, before, during or after such treatment, with a composition containing protective agents.

This invention is related to that disclosed in U.S. Pat. No. 4,818,245 which is assigned to the same company as this case.

U.S. Pat. No. 4,371,517, to Vanlerberghe et al, describes the use of a combination of a cationic polymer, an anionic polymer, an alkali metal salt, and a non-ionic surfactant which contains carboxyl or carboxylated groups in compositions to be used to wash or dye hair. Copolymers containing tetraalkyl ammonium halide units are disclosed at column 4.

U.S. Pat. No. 4,645,663 to Grollier et al deals with hair dyeing or bleaching compositions which contain copolymers having tetralklyammonium halide units (see column 9).

Both of these patents refer to treatment systems in which maximum conditioning effectiveness requires the conjoint use of either an anionic polymeric component or an anionic surfactant with the cationic copolymers.

Sokol U.S. Pat. Nos. 3,912,808 and 3,986,825 disclose similar systems of cationic copolymers in which surfactant is either present in the compositions or used in post-treatments.

The disclosures of the above-referenced patents are hereby incorporated by reference.

THE INVENTION

The invention deals with compositions and processes for conditioning hair or other proteinaceous substrates.

Applicants have discovered that the treating of hair or other proteinaceous substrates with compositions containing a copolymer of about 10% hexadecyldimethylpropyl methacrylamide ammonium bromide (HDPM) with about 90% methylacrylamidopropyltrimethyl ammonium chloride (MAPTAC), which copolymers are referred to as "H-QUAT" polymers, with other chemical treating materials, e.g., coloring, bleaching, perming and/or shampooing compositions, made the hair more easily combable and manageable.

ADVANTAGES

The compositions of the invention have several advantages over known compositions and processes for treating hair and other fibrous substrates to render them more manageable and to stabilize them against the harsh side effects of chemical processing.

One major advantage resides in the fact that compositions containing cationic H-QUAT polymers need not be used in conjunction with anionics in order to effect beneficial results. Thus, unlike other systems described above, the cationics can be used in one-step conditioning as the sole polymeric agents in the protective compositions and processes of the invention.

Note that many cationic/anionic combinations result in "over conditioning" problems when the polymer precipitates into the hair. Such problems are minimized using the instant system. In fact, the "over conditioning" which is typical with the use of cationic/anionic complexes or combinations is virtually eliminated using the instant invention because no anionic polymer or surfactant complexes or combinations are needed for the operability of the invention.

In addition, the high miscibility of these cationic polymers with aqueous solvents and other polar liquids make their formulation both easy and inexpensive.

Furthermore, the compositions and processes of the invention produce improvements in the treated hair e.g. less tangling and static and better feel. These improvements are durable, generally lasting through several, e.g. 2–5, shampoos.

These and other aspects and advantages of the invention will become more apparent after consideration of the following description of the invention.

DESCRIPTION OF THE INVENTION

The invention is concerned with novel polymeric compositions for treating proteinaceous or other fibrous substrates and to processes involving the use of those compositions.

Compositions

The compositions of the invention containing, as essential components, cationic polymers of a particular type and one or more carriers.

Cationic polymers

The cationic polymers employed herein are generally copolymers of acrylic and or methacrylic species. Preferably they are (meth)acrylic copolymers containing a significant percentage, i.e. at least 1% fatty substituted trialkyl ammonium halide units of formula I:

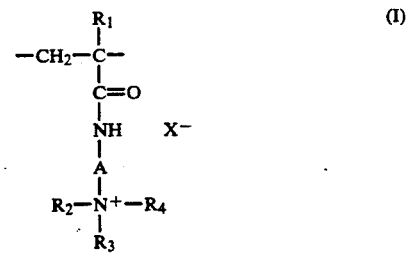

wherein $R_1$ is H or $CH_3$;

A is a $C_1$–$C_5$ alkylene linkage $R_2$ is $C_{10}$–$C_{25}$ alkyl, $R_3$ and $R_4$ are each independently selected from, $C_{1-6}$ alkyl groups, and X is Cl, or Br.

These units are copolymerized with units of formula II as follows:

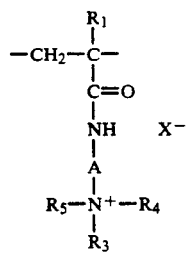

wherein $R_5$ is a $C_{1-6}$ alkyl group, $R_1$, A, $R_3$, $R_4$ and X are as defined above for formula I.

Preferably, the copolymer employed are those which contain from about 1 to about 20 mole %, preferably about 5 to about 15 mole %, most preferably about 10 mole % of units of formula I and about 20 to about 99 moles %, preferably about 85 to 95%, most preferably about 90 mole % of units of formula II. One particularly preferred polymer of this type is the "H-Quat" polymer which contains 10% hexadecyldimethylpropylmethacrylamide ammonium bromide (HDPM) and 90% methacrylamidopropyltrimethyl ammonium chloride.

While units of formulas I and II are essential in the cationic species to be used, the presence of other vinyl residues is contemplated. Thus, useful copolymers may contain moieties derived from one or more other unsaturated species, such as ethylene, propylene, $C_{1-6}$ (meth)acrylates, $C_{1-6}$ (meth)acrylamides, and the like.

These polymeric component(s) may be used in combination with other polymers. However, no other polymers need be present. The polymeric components of applicants' composition are cationic polymers which requires no additional anionic or nonionic species for "balance". While applicants' copolymers are within the broad grouping of polymers disclosed in U.S. Pat. Nos. 4,371,517 and 4,645,663 the sole use of the specific polymers described above for applicants' purposes is not taught therein.

Although anionic surfactants are not required for effect in the product, their use is not precluded.

The compositions of the invention are generally applied from a liquid or spray formulations. Optionally, they may be formulated into gels, creams, or other forms.

Diluents

The compositions of the invention contain one or more diluents or carriers. Typically, the carrier employed will be aqueous, e.g. water alone, or water/$C_{1-3}$ alcohol combinations, or $C_{1-3}$ alcohols alone.

Applicants' treatment compositions contain from about 0.05 to about 1 wt. %, preferably about 0.2 to about 0.5 wt. %, of one or more polymeric additive(s), with the remainder being one or more carrier(s) or other conventional additives.

Conventional excipients or additives may be used in suitable quantities in the compositions of the invention. Thus, depending upon the overall function of the treating composition, one or more surfactants, plasticizers, soaps, stabilizers, fillers, thixotropic agents, colorants, perfumes, buffers and the like may be employed.

When the polymeric components of the invention are used in post-shampoo rinses, e.g. in conditioning formulations, they will be present at concentration levels of about 0.05 to about 5 wt. % preferably about 1 to about 1.5wt. %.

Hair Treatment

The compositions of the invention can be applied to proteinaceous substrates of a variety of types. While the treatment of hair on the human head is highly preferred, the compositions can also be used to treat hair which is not on a body, e.g. in wigs, swatches, garments made of hair, etc. It may also be applied to non-human hair or fur, e.g., wool or dog hair as well as pelts o skins of other animals.

Alternatively, the compositions can be used to treat keratin fibers such as hair and wool. Blends, e.g., polymer/wool, can also be present in substrates to be treated.

These compositions are usually applied in any suitable liquid form such as sprays, lotions or creams. Thus, they can be formulate using the carrier(s) and/or other excipients discussed above in order to achieve requisite properties, e.g. viscosity, stability, handling properties, etc.

While liquid formulations are preferred, the use of semi-solids and solids is contemplated. Thus, gels, mousses, creams as well as hot melt formulations are envisioned.

When a liquid formulation is sprayed onto the hair it is visually used in the form of a solution of the polymeric component in a carrier such as water or mixtures of water and ethanol.

In the preferred embodiment, the composition is applied one or more times via spraying from a conventional non-aerosol spray device onto the hair or other substrate to deposit about 0.01 to about 0.02 g. of polymer on a typical head of hair. The chemical treatment is then applied without attempting to rinse the hair. Shampooing may be done after the chemical treatment is used.

While it is preferred that the compositions be applied before any chemical treatment, i.e., as pre-treatment compositions, they may also be used during, and/or after the use of conventional chemical agents.

EXAMPLES

The following examples are given to further illustrate the present invention. Compositions were prepared comparing H-Quat, poly(methacrylamidopropyltrimethyl ammonium chloride (PMAPTAC), polyquaternium 10 and polyquaternium 6 as the actives and applied to hair previously tinted and therefore usually difficult to comb and hard to manage. The compositions were applied in the form of a spray.

EXAMPLES I

Hair Tint Composition I was mixed with 20 volume hydrogen peroxide and applied immediately thereafter. It was allowed to remain on hair swatches of 2 g. size for 30 minutes and rinsed off. Two controls were not pre-treated. One of these controls was post-treated with a Standard Conditioner Composition (Composition E) which is the usual method for conditioning hair.

| HAIR TINT COMPOSITION I | PERCENT |
| --- | --- |
| P-Phenylenediamine | 2.20 |
| Resorcinol | 1.10 |
| M-aminophenol | 1.00 |
| Sodium Sulfite | 0.10 |
| EDTA | 0.05 |
| Propylene Glycol | 5.00 |
| Isopropanol | 10.00 |

| HAIR TINT COMPOSITION 1 | PERCENT |
|---|---|
| Nonoxynol-4 | 3.50 |
| Cetyl Alcohol | 5.00 |
| Ammonium Hydroxide | 9.00 |
| Ceteareth-20 | 3.50 |
| Water | 59.45 |
| TOTAL | 100.00 |

The following conditioning compositions were used to pre-treat the hair swatches:

| | Percent |
|---|---|
| Composition A | |
| H-Quat | 0.24 |
| Water | 99.76 |
| Composition B | |
| POLYMAPTAC | 0.24 |
| Water | 99.76 |
| Composition C | |
| Polyquaternium 10 | 0.24 |
| Water | 99.76 |
| Composition D | |
| Polyquaternium 6 | 0.24 |
| Water | 99.76 |
| Standard Conditioner Composition (Composition E) | |
| Ceteareth-20 | 3.5 |
| Cethyl Alcohol | 1.0 |
| Strealkonium Chloride | 2.0 |
| Citric Acid | 3.0 |
| Water | 90.5 |
| | 100.0 |

The swatches were rinsed and then evaluated for ease of wet combing before shampooing and after lathering with shampoo. A scale was used with the untreated control assigned zero and the control post treated with standard conditioner composition E assigned 5.

Table I clearly illustrates the efficacy and durability of H-Quat.

TABLE I

Combability of tinted hair (1) immediately after treatment with conditioner and (2) after three latherings with shampoo*.

| Composition | Before Shampooing | After 3 Latherings |
|---|---|---|
| A. H-Quat | 4.0 | 4.0 |
| B. POLYMAPTAC | 1.5 | 0.0 |
| C. Polyquaternium 10 | 0.0 | 0.0 |
| D. Polyquaternium 6 | 1.5 | 0.0 |
| E. Standard Conditioner Composition | 5.0 | 0.0 |
| Control | 0.0 | 0.0 |

*The shampoo used was condition* Shampoo from Clairol.

EXAMPLE II

Previously tinted hair was permed with the following composition:

| PERM COMPOSITION FOR TINTED HAIR | PERCENT |
|---|---|
| Ammonium Thioglycolate (60% as acid) | 12.2 |
| Laureth-23 | 1.5 |
| Fragrance | 1.0 |
| EDTA | 0.1 |
| Ammonium Hydroxide | 3.5 |
| Water | 81.7 |
| TOTAL | 100.0 |

The perm composition was neutralized with 2.0% Hydrogen Peroxide.

Prior to perming, swatches of the size used above were treated with the compositions of A-D in the same manner. Two control swatches were made without a pre-treatment. One of the controls was post-treated with Standard Conditioner Composition E. The swatches were then evaluated for ease of wet combing after neutralization of the perm and after three lathers with Condition* Shampoo by Clairol.

A combability scale was assigned with the untreated control assigned zero and the control post treated with Standard Conditioner Composition was assigned 5. Table II clearly illustrates the results.

TABLE II

Combability of tinted permed hair (1) immediately after treatment with conditioner and (2) after three latherings with shampoo

| Composition | Before Shampooing | After 3 Latherings |
|---|---|---|
| A. H-Quat (Example I) | 4.5 | 4.5 |
| B. Polympatac (Example II) | 2.5 | 0.0 |
| C. Polyquaternium 10 (Example III) | 0.0 | 0.0 |
| D. Polyquaternium 6 (Example IV) | 3.0 | 1.0 |
| E. Standard Conditioner Composition | 5.0 | 0.0 |
| Control | 0.0 | 0.0 |

Conditioning occurs during the chemical treatment and persists after the hair is washed and styled.

EXAMPLE III

To further illustrate the invention, the compositions A-D were applied prior to the application of A Standard Hair Straightening Composition. The straightener was left on ten minutes and then rinsed.

| STANDARD HAIR STRAIGHTENER | PERCENT |
|---|---|
| Water | 74.25 |
| Propylene Glycol | 2.00 |
| Mineral Oil | 10.00 |
| Emulsifying Wax NF | 5.00 |
| Laneth-15 | 1.00 |
| Cetyl Alcohol | 1.00 |
| Ceteareth-20 | 3.00 |
| Laneth 5 and Ceteth-25 | 2.00 |
| Sodium Hydroxide | 1.75 |
| TOTAL | 100.00 |

Two control swatches of the same size as those used above were made. One swatch was only treated with Standard Hair Straightener and the other was post-treated with Standard Conditioning Composition E. The swatches were evaluated for ease of wet combing. A scale of 0 to 5 was used with the control assigned 0 and the swatch post treated with Standard Conditioning Composition assigned 5. The results are set out in Table III.

TABLE III

Combability of Hair Post-Straightened after treatment with conditioner with combability measured, before and after shampooing

| Composition | Before Shampooing | After 3 Latherings |
|---|---|---|
| A. H-Quat | 5.0 | 4.0 |
| B. POLYMAPTAC | 3.5 | 2.0 |
| C. Polyquaternium 10 | 1.0 | 0.0 |
| D. Polyquaternium 6 | 3.5 | 2.0 |
| E. Standard Conditioner | | |
| Composition | 5.0 | 0.0 |
| Control | 0.0 | 0.0 |

The foregoing examples have illustrated the ability of H-Quat to condition without the necessity of complexing with an anionic surfactant and its improved durability by surviving various processing steps and subsequent shampooings.

Reasonable variations, such as those which would occur to a skilled artisan, can be made herein without departing from the scope of the invention.

We claim:

1. A method of treating a proteinaceous substrate to render it more easily combed when wet comprising the step of applying to the substrate a composition consisting essentially of:
   (a) water, and
   (b) a cationic copolymer which contains, on a mole basis, about 1% to about 20% hexadecyldimethylpropylmethacrylamide ammonium halide and about 80% to about 99% methacrylamidopropyltrimethyl ammonium halide,
   wherein the halide is selected from the group consisting of chloride and bromide.

2. The method of claim 1 wherein the substrate is human hair.

3. The method of claim 2 wherein the cationic polymer contains, on a mole basis, about 10% hexadecyldimethylpropylmethacrylamide ammonium bromide and 90% methacrylamidopropyltrimethyl ammonium chloride.

4. A method of conditioning and coloring a proteinaceous substrate comprising the steps of:
   (a) pretreating the substrate with a one-step conditioning composition consisting essentially of a cationic polymer which contains, on a mole basis, about 1% to about 20% of hexadecyldimethylpropylmethacrylamide ammonium halide and about 80% to about 99% methacrylamidopropyltrimethyl ammonium halide; and
   (b) applying a hair coloring composition to the substrate, wherein the pretreatment of step (a) improves wet combability, and
   wherein the halide is selected from the group consisting of chloride and bromide.

5. The method of claim 4 wherein the substrate is human hair.

6. The method of claim 5 wherein the cationic polymer contains, on a mole basis, about 10% hexadecyldimethylpropylmethacrylamide ammonium bromide and 90% methacrylamidopropyltrimethyl ammonium chloride.

* * * * *